(12) United States Patent
Sunami et al.

(10) Patent No.: US 8,797,533 B2
(45) Date of Patent: Aug. 5, 2014

(54) DEPOLARIZER AND CIRCULAR DICHROISM SPECTROMETER USING THE SAME

(71) Applicant: JASCO Corporation, Hachioji (JP)

(72) Inventors: Tetsuji Sunami, Hachioji (JP); Keisuke Watanabe, Hachioji (JP); Jun Koshobu, Hachioji (JP)

(73) Assignee: JASCO Corporation, Tokyo (JP)

( * ) Notice: Subject to any disclaimer, the term of this patent is extended or adjusted under 35 U.S.C. 154(b) by 0 days.

(21) Appl. No.: 13/727,709

(22) Filed: Dec. 27, 2012

(65) Prior Publication Data

US 2013/0169965 A1 Jul. 4, 2013

(30) Foreign Application Priority Data

Dec. 28, 2011 (JP) ................................. 2011-287105

(51) Int. Cl.
*G01J 4/00* (2006.01)
(52) U.S. Cl.
USPC .......................................... 356/364; 356/367
(58) Field of Classification Search
USPC .............. 356/364–370, 128–137; 359/494.01
See application file for complete search history.

(56) References Cited

FOREIGN PATENT DOCUMENTS

| JP | 6-317518 | 11/1994 |
| JP | 09-269411 | 10/1997 |
| JP | 2006-39076 | 2/2006 |
| WO | 2006/131517 A2 | 12/2006 |

OTHER PUBLICATIONS

European Search Report for corresponding EP 12199549 mailed May 2, 2013, six pages.
Patent abstract and machine translation for JP Publication No. 06-317518 published Nov. 15, 1994, 13 pages.
Patent abstract and machine translation for JP Publication No. 2006-039076 published Feb. 9, 2006, 55 pages.
Patent Abstracts of Japan, Publication No. 06-317518 (corresponding publication of JP 3341928), 12 pages, Nov. 15, 1994.
Patent Abstracts of Japan, Publication No. 09-269411, 9 pages, Oct. 14, 1997.

*Primary Examiner* — Tri T Ton
(74) *Attorney, Agent, or Firm* — Rankin, Hill & Clark LLP

(57) ABSTRACT

A depolarizer includes a pair of wedge-shaped plates made of an optically isotropic material, laid one on top of another such that the total thickness is constant and wedge-plate holding means for holding the pair of wedge plates separately. The wedge-plate holding means includes a pressure-applying section for applying pressure to each of the pair of wedge plates in a direction perpendicular to the thickness direction of the pair of wedge plates. The pressure-applying direction for one of the pair of wedge plates and the pressure-applying direction for the other of the pair of wedge plates intersect at an angle of 45 degrees.

13 Claims, 4 Drawing Sheets

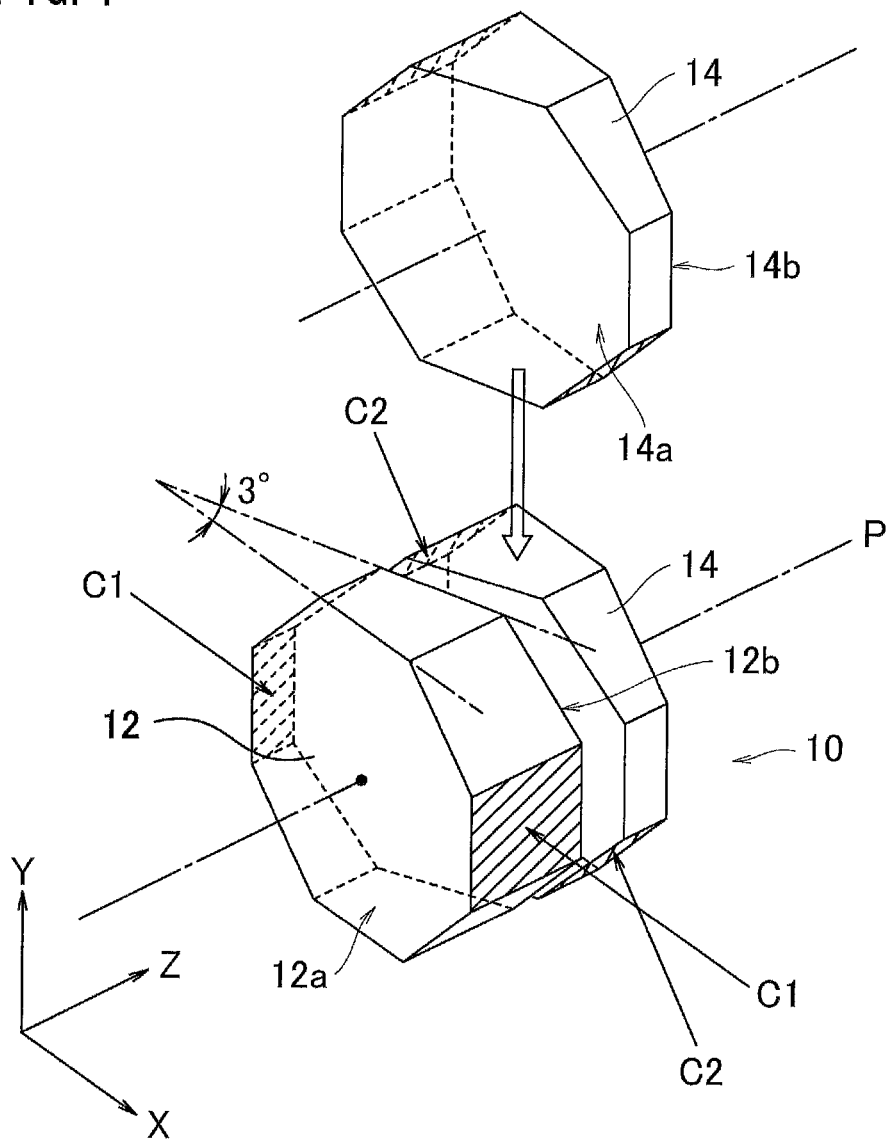

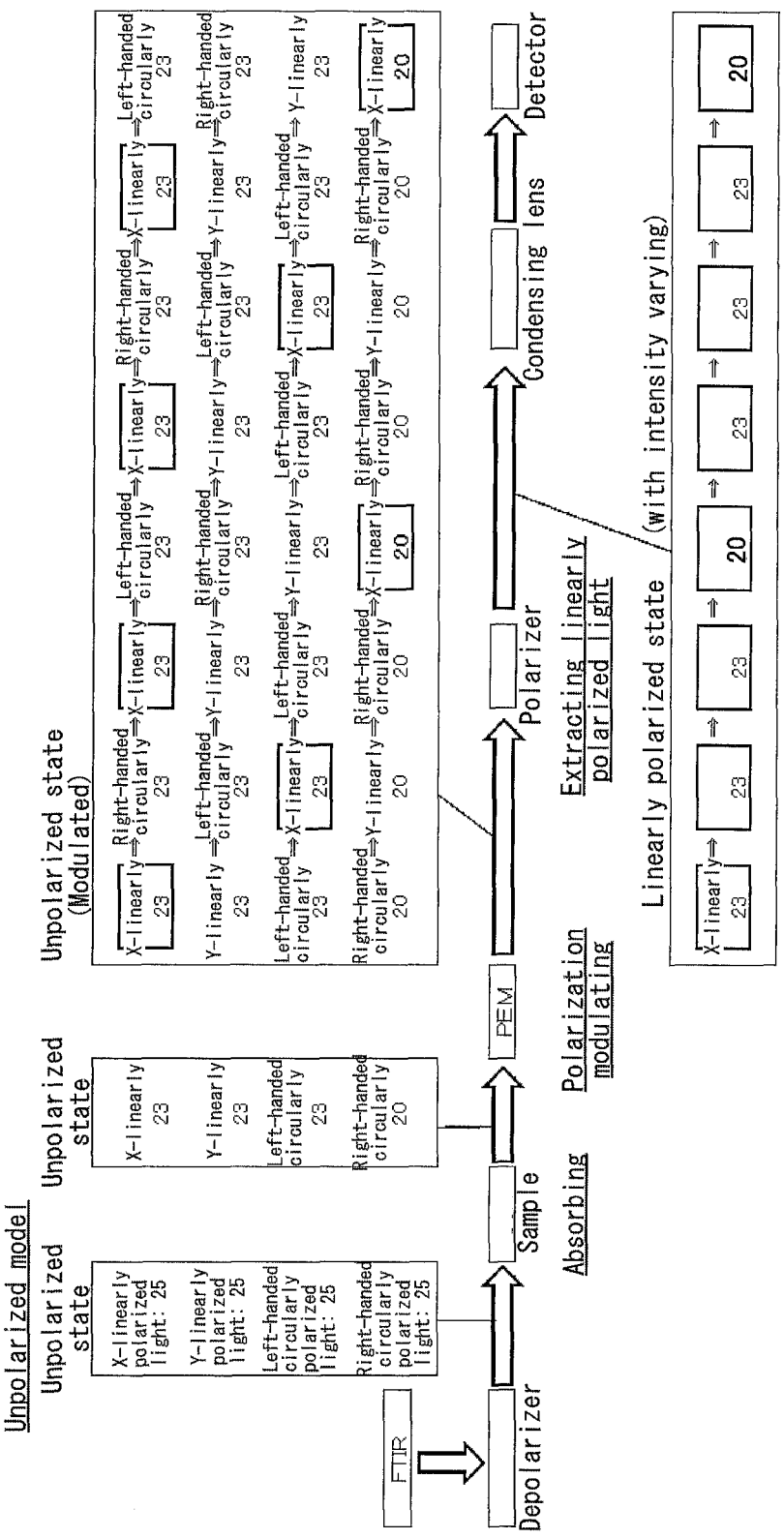

DEPOLARIZER AND CIRCULAR DICHROISM SPECTROMETER USING THE SAME

CROSS-REFERENCE TO RELATED APPLICATIONS

This application is based on and claims the benefits of priority from Japanese Patent Application No. 2011-287105, filed on Dec. 28, 2011, the entire contents of which are incorporated herein by reference.

BACKGROUND OF THE INVENTION

1. Field of the Invention

The present invention relates to improvements in depolarizers and improvements in circular dichroism (CD) spectrometers in terms of accuracy.

2. Description of the Related Art

Circular dichroism (CD) spectrometry has been widely used as virtually the only spectroscopic method for analyzing the three-dimensional structures of molecules directly. The method was initially used to determine absolute structures of bioactive natural organic compounds and in the stereochemical study of complex compounds, and was subsequently used in biochemistry to analyze the high-order structures of biological polymers such as proteins. The method has been very useful to measure the thermal stability of biological polymers and to analyze the reaction processes of enzyme reactions, for example. In the pharmacology and pharmaceutical industry, the method has been indispensable to reduce side effects by analyzing molecular asymmetry and medical effects and to control the activity of enzymes incorporated in drugs and the like.

CD spectrometers are broadly divided into ECD spectrometers for measuring primarily circular dichroism related to electron transitions in the ultraviolet, visible, or near-infrared region and VCD spectrometers for measuring primarily circular dichroism related to vibrational transitions in the infrared region. Since a spectrum obtained by measurement is close to a spectrum predicted in calculation from a molecular structure, the application of VCD spectrometers is expanding to the structural analysis of drugs and biologically active substances.

In a conventional CD spectrometer, a polarizer transmits only light having a specific linear polarization included in a light beam coming from a light source; a photoelastic modulator modulates the linearly polarized light alternately into a right-handed circularly polarized light beam and a left-handed circularly polarized light beam; and the right-handed and left-handed circularly polarized light beams are alternately directed onto a sample. Because of the difference in absorbance of right-handed and left-handed circularly polarized light beams in the sample due to the properties of the sample, the intensity of light transmitted through the sample depends on the right-handed or left-handed rotating of circularly polarized light. A detector detects the intensity of light transmitted through the sample, and signal processing means calculates the difference in absorbance between the right-handed and left-handed circularly polarized light beams, that is, circular dichroism on the basis of variations in the light intensity signal of the transmitted light. Through that process, the internal structure and other properties of the sample are investigated.

PATENT LITERATURE

Patent Literature 1: Japanese Patent No. 3341928
Patent Literature 2: Japanese Unexamined Patent Application Publication No. H9-269411

SUMMARY OF THE INVENTION

The optical components included in the conventional CD spectrometer, such as the photoelastic modulator and a lens disposed before the detector, have some distortion. Birefringence resulting from the distortion of an optical component can change the polarization state, causing a circular dichroism measurement error to occur. To reduce the measurement error resulting from the distortion of an optical component, a depolarizer is added to the optical configuration of the conventional spectrometer so that light is brought into an unpolarized state before it is directed onto the sample (Patent Literature 1).

One known depolarizer is configured by joining two wedge-shaped plates made of a birefringent material, that is, anisotropic crystal. Another known depolarizer is formed by joining four birefringent wedge-shaped plates (Patent Literature 2). In those conventional depolarizers, the wedge-shaped plates are formed in such a manner that the directions of optical axes of the anisotropic crystals are different when the plates are joined. Since incident light has some breadth in its cross section, light rays transmitted by the depolarizer differ in phase, depending on variations in thickness of the wedge-shaped plates. Accordingly, the transmitted rays are polarized depending on their incident positions on the depolarizer. The polarization states depending on the incident positions are different each other. Thus, the entire light beam is a mixture of a variety of polarization states, and the obtained light appears to be unpolarized.

The inventors have diligently studied depolarizers having new configurations and have strived to create a depolarizer having a simple configuration without using a birefringent anisotropic crystal material used in the related art. Accordingly, it is an object of the present invention to provide a depolarizer having a simple configuration without using a birefringent anisotropic crystal material. Another object is to provide a circular dichroism spectrometer using the depolarizer.

Means for Solving the Problems

A depolarizer in the present invention includes a pair of wedge-shaped plates made of an optically isotropic material, laid one on top of another such that the total thickness is constant and wedge-plate holding means for holding the pair of wedge plates separately. The wedge-plate holding means includes a pressure-applying section for applying pressure to each of the pair of wedge plates in a direction perpendicular to the thickness direction of the pair of wedge plates. The pressure-applying direction for one of the pair of wedge plates and the pressure-applying direction for the other of the pair of wedge plates intersect at an angle of 45 degrees.

It is preferable that the pressure-applying direction for the one of the pair of wedge plates be parallel to the direction in which the thickness of the wedge plate changes at the maximum rate.

It is preferable that the pressure-applying section include a fixed member and a holding member for holding each of the pair of wedge plates, and the holding member be provided to be movable in the pressure-applying direction with respect to the fixed member.

It is preferable that the optically isotropic material be an optically isotropic crystal such as ZnSe.

It is preferable that each of the pair of wedge plates has the shape of a regular octagon when viewed from the thickness direction.

A circular dichroism spectrometer according to the present invention includes a polarizer which transmits light having a specific linear polarization in a light beam coming from a light source, a polarization modulator which generates right-handed circularly polarized light and left-handed circularly polarized light alternately by modulating the linearly polarized light, a sample setting portion which is alternately exposed to the right-handed circularly polarized light and the left-handed circularly polarized light, the depolarizer which is disposed after the sample setting portion to depolarize the beam reflected or transmitted by the sample setting portion, and a detector which detects the intensity of the depolarized light. The detector obtains a difference in absorbance between the right-handed circularly polarized light and the left-handed circularly polarized light in accordance with a change in the detected intensity of light.

It is preferable that a focusing lens for focusing light be disposed before the detector and that the depolarizer be disposed before the focusing lens.

A circular dichroism spectrometer according to the present invention includes the depolarizer which is disposed after a light source to depolarize a light beam coming from the light source, a sample setting portion which is exposed to the depolarized light beam, a polarization modulator which modulates light reflected or transmitted by the sample setting portion, a polarizer which transmits linearly polarized light having a specific polarization plane in the modulated light beam, and a detector which detects the intensity of the linearly polarized light. The detector obtains a difference in absorbance between right-handed circularly polarized light and left-handed circularly polarized light in the depolarized light beam in accordance with variations in the detected intensity of light.

It is preferable that the depolarizer be switchable in accordance with the measurement wave number range.

BRIEF DESCRIPTION OF THE DRAWINGS

FIG. 1 is a perspective view illustrating major components of a depolarizer according to the present invention.

FIG. 5 is a diagram illustrating the advantages of the circular dichroism spectrometer according to the above embodiment.

DESCRIPTION OF THE PREFERRED EMBODIMENTS

Depolarizer

Figure 2A:
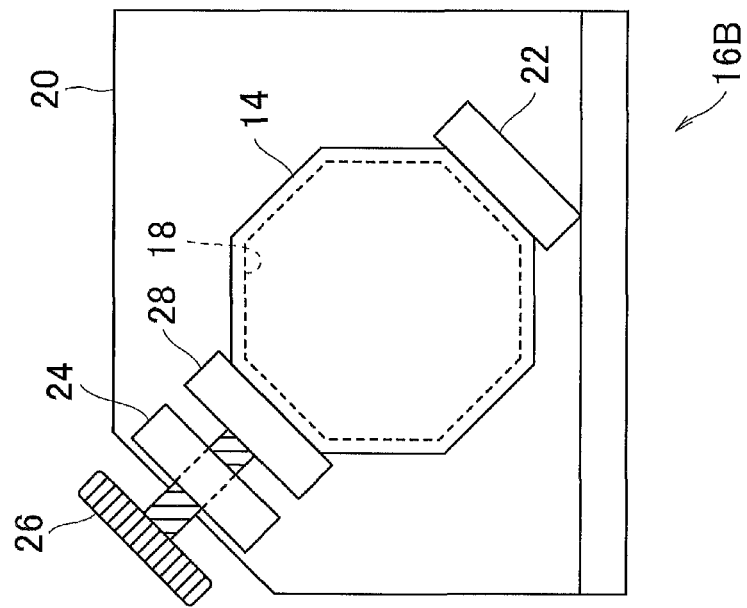
FIGS. 2A and 2B illustrate the structures of holders for wedge plates in the depolarizer.

A depolarizer according to an embodiment of the present invention will be described with reference to FIG. 1. The figure is a perspective view of an example of the depolarizer. The depolarizer 10 includes two wedge-shaped, optically isotropic crystal (ZnSe, for example) plates 12 and 14 and holders 16 (corresponding to wedge-plate holding means; see FIG. 2) for holding the wedge plates 12 and 14 separately.

The wedge plates 12 and 14 appear as a regular octagon when viewed from the Z-axis direction and have the shape of a wedge whose thickness in the Z-axis direction varies with the position in the X-axis direction when viewed from the Y-axis direction. The back face is inclined with respect to the front face. The front face 12a and the back face 12b of the wedge plate meet at an angle of 3 degrees, for example. A light beam having a certain breadth and passing through the wedge plate includes light passing through the longest optical path and light passing through the shortest optical path. If the wedge plate has birefringent properties, the degree of depolarization differs depending on the difference in optical path length. A single wedge plate that does not produce a certain level of difference in optical path length would provide insufficient depolarization. The degree of depolarization, which will be described later, depends on the wavelength of incident light and the birefringent properties of the wedge plates, as well as the difference in optical path length. For example, in a wedge plate provided to depolarize infrared light, if the cross section of the incident light has a diameter of about 25 mm, the effective distance between the opposite sides of the regular octagonal shape of the wedge plate is not less than about 25 mm, and an intersection angle of 3 degrees or more is required.

The shape of the front faces of the wedge plates 12 and 14 are not confined especially, but a regular octagon as shown in FIG. 1 is preferable. The regular octagon is preferred because pressure can be easily applied to faces of the wedge plates 12 and 14 and because the wedge plates 12 and 14 can be rotated to change their attitude when necessary. Moreover, since the two wedge plates 12 and 14 have the same shape and are made from optically isotropic crystals, the front wedge plate 12 and the back wedge plate 14 do not have to be distinguished, allowing them to be handled easily. In addition, identical wedge-plate holding means can be used for the two wedge plates.

The holders 16 hold the wedge plates 12 and 14 in such a manner that one wedge plate is laid on top of another and the total thickness of the two wedge plates is constant. In this embodiment, a space is left between the two wedge plates, in order to apply pressure to each wedge plate appropriately. It is possible to leave no space between the wedge plates if leaving no space does not conflict with the structure of the holders 16 and applying pressure to the wedge plates 12 and 14.

The holders 16 apply pressure to the front wedge plate 12 in the C1 direction and the back wedge plate 14 in the C2 direction. The front face 12a of the front wedge plate 12 and the rear face 14b of the back wedge plate 14 are parallel. The light beam to be depolarized is incident on one of the faces at a right angle. The optical axis of incident light is denoted by P in the figure. The directions C1 and C2 in which pressure is applied are perpendicular to the optical axis P of incident light.

In this embodiment, the pressure-applying direction C1 for the front wedge plate 12 matches the direction of the largest inclination of the front wedge plate 12. The angle at which the pressure-applying direction C1 intersects with the pressure-applying direction C2 for the back wedge plate 14 is 45 degrees when viewed from the Z-axis direction. The direction of the largest inclination of the wedge plate 12 or wedge plate 14 is a direction which is perpendicular to the optical axis P of incident light and in which the inclination of the inclined face 12b or 14a of the wedge plate becomes largest. In FIG. 1, the direction of the largest inclination of both wedge plates matches the X-axis direction. The direction of the largest inclination is also called the direction of the maximum rate of change in thickness of the wedge plate.

The two pressure-applying directions C1 and C2 are not limited to the combination shown in FIG. 1. In the present invention, as the minimum requirements, the two pressure-applying directions should be perpendicular to the optical axis P of incident light and should intersect with each other at an angle of 45 degrees. The direction of the optical axis P of incident light is also the thickness direction between the front face 12a of the wedge plate 12 and the rear face 14b of the wedge plate 14 in the pair of wedge plates 12 and 14.

Specific configurations of the holders 16 will be described next with reference to FIGS. 2A and 2B. FIG. 2A shows a front view of the holder 16A from the Z-axis direction and a plan view from the Y-axis direction. The holder 16A shown in FIG. 2A is for the front wedge plate 12 and includes a base 20 having an octagonal window 18, a fixed plate (fixed member) 22, a screw holding plate 24, a set screw 26 screwed into the screw holding plate 24, and a pressing plate (pressing member) 28 mounted at the tip of the set screw 26. The fixed plate 22 and the pressing plate 28 are disposed on the opposite sides of the window 18, The fixed plate 22 aligns the wedge plate 12 with the window 18. The pressing plate 28 moves back and forth with respect to the fixed plate 22 as the set screw 26 rotates. When the set screw 26 is screwed into the screw holding plate 24, the wedge plate 12 is held between the fixed plate 22 and the pressing plate 28. A predetermined compressive stress can be applied to the wedge plate 12 by adjusting the torque of the set screw 26. The fixed plate 22 and the pressing plate 28 correspond to the pressure-applying section of the present invention.

The wedge plates 12 and 14 are made from zinc selenide (ZnSe) crystals having no optical anisotropy. Since the wedge plates 12 and 14 have the shape of a regular octagon when viewed from the Z-axis direction, they have four pairs of parallel faces around the regular octagon. When mechanical pressure is applied perpendicularly to one pair of parallel faces by the pressing plate 28 and the fixed plate 22, optical anisotropy occurs in the pressure-applying direction and in its orthogonal direction, causing the wedge plates 12 and 14 to start functioning as phase retarders. Since the optical anisotropy of the wedge plates 12 and 14 can be adjusted according to the magnitude of the mechanical pressure, a phase difference δ should be measured and adjusted to depolarize light linearly polarized at 45 degrees from the pressure-applying direction. Rays with different phase differences are spatially distributed in the incident light, and it would be difficult to determine a specific phase difference δ. For example, it is advisable to adjust the pressure to bring the phase difference δ close to the wavelength of the incident light.

With the holder 16A, the front wedge plate 12 can be compressed in the direction C1 of the largest inclination of the front wedge plate 12.

Figure 2B:
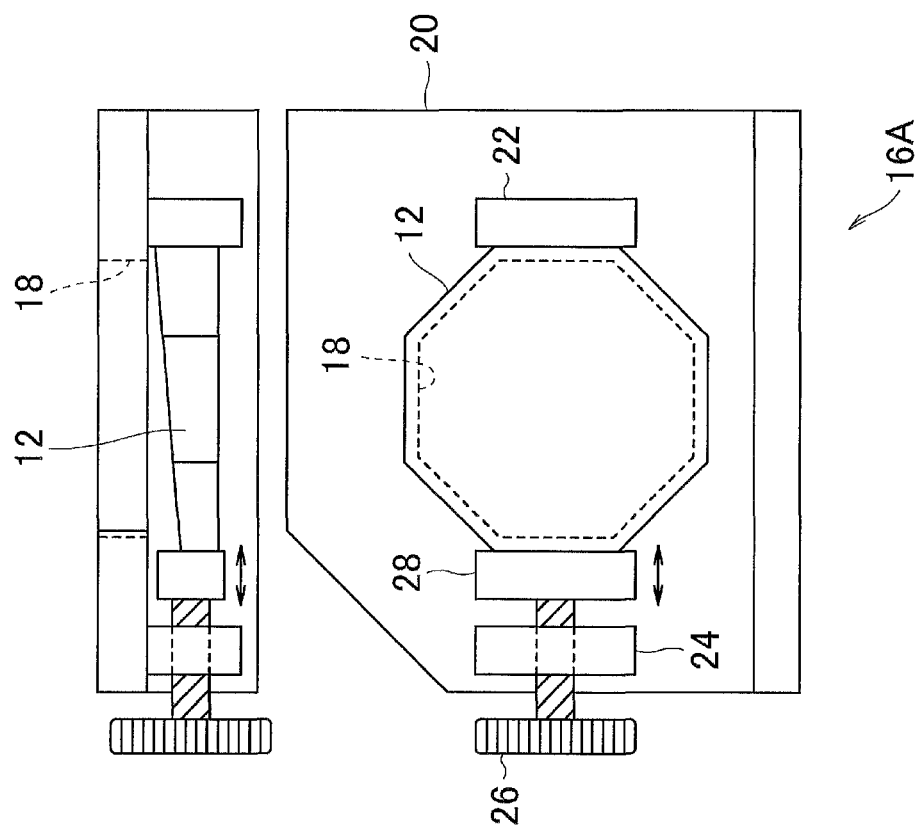

The holder 16B shown in FIG. 2B is for the back wedge plate 14 and includes the same components as included in the holder 16A shown in FIG. 2A. However, the positions of the fixed plate 22 and the pressing plate 28 with respect to the window 18 of the base 20 are different. In the holder 16A shown in FIG. 2A, the fixed plate 22 and the pressing plate 28 are disposed to sandwich the wedge plate 12 in the horizontal direction. In the holder 16B shown in FIG. 2B, the fixed plate 22 and the pressing plate 28 are disposed to sandwich the wedge plate 14 in a direction crossing the horizontal direction at an angle of 45 degrees.

With the holder 16B, the back wedge plate 14 can be compressed in the direction C2 at an angle of 45 degrees to the direction of the largest inclination of the back wedge plate 14. The holder 16A shown in FIG. 2A and the holder 16B shown in FIG. 2B are merely examples. Other holders that can apply pressure to the wedge plates 12 and 14 separately in the directions C1 and C2 may also be used. For example, a holder that can apply pressure to both the wedge plate 12 and the wedge plate 14 may be used.

The depolarization of incident light by the depolarizer 10 configured as described above will be described next with reference to FIG. 1. The wedge plates 12 and 14 compressed respectively with the holders 16A and 16B serve as optically anisotropic phase retarders. The anisotropic optical axes of the two wedge plates 12 and 14 intersect with each other at an angle of 45 degrees. In the Cartesian X-Y-Z coordinate system, the Z-axis being the optical axis P of incident light and the X-axis being the anisotropic optical axis of the front wedge plate 12, as shown in FIG. 1, the anisotropic optical axis of the back wedge plate 14 is in the direction expressed as Y=−X.

In the following description, incident light on the front wedge plate 12 will be resolved into an X-direction vibration component Ex and a Y-direction vibration component Ey. Because of their different refractive indices, the vibration components Ex and Ey cause a phase shift to occur in the front wedge plate 12, depending on the thickness of the wedge plate 12. If light incident on the front wedge plate 12 is linearly polarized light with a polarization plane (vibration plane) expressed as Y=X, the phase difference δ between the vibration components Ex and Ey increases as the thickness of the wedge plate 12 at the position of incidence increases. The phase difference δ determines the polarized state. For example, as the phase difference δ of the vibration components increases, Y=X linearly polarized light changes to right-handed circularly polarized light, then through Y=−X linearly polarized light to left-handed circularly polarized light.

Since the thickness of the front wedge plate 12 continuously varies in the X direction, the phase difference δ given according to the position in the X direction also varies continuously. If incident light of a single polarization state has even a small breadth in the X direction, light beams transmitted by the depolarizer 10 have a variety of polarization states depending on the position in the X direction. The mixture of the variety of polarization states produces a certain type of unpolarized state, and the entire light beam can be considered to have been depolarized.

Moreover, since the anisotropic optical axes of the front wedge plate 12 and the back wedge plate 14 intersect with each other at an angle of 45 degrees, linearly polarized incident light with a polarization plane in any direction can be depolarized. If the polarization direction of linearly polarized incident light agrees with the anisotropic optical axis (X direction) of the front wedge plate 12, the incident light passes through the front wedge plate 12 without being depolarized. The polarization direction of the linearly polarized incident light and the anisotropic optical axis of the back wedge plate 14 meet at an angle of 45 degrees, and the maximum depolarization effect is provided by the back wedge plate 14. The depolarizing effect of the depolarizer 10 in the present invention varies a little with the polarization direction of the incident light, but a certain level of depolarization can be obtained in any direction.

First Embodiment

A circular dichroism (CD) spectrometer 100 according to a first embodiment of the present invention will be described with reference to FIG. 3, which shows the entire configuration of the CD spectrometer 100.

The measuring optical system includes a Fourier transform infrared spectrometer (FTIR) 20, an optical filter 30, a polarizer 40, a polarization modulator (PEM 50), a sample setting portion 60, a depolarizer 10, a focusing lens 70, and a detector 80. Those components are disposed on the optical axis of the test beam in that order.

The FTIR 20 is a general infrared spectrometer based on a Michelson interferometer including a movable mirror and produces output beams, generating an interferogram. The interferometer in the FTIR 20 includes a beam splitter which splits infrared light into two beams. One split beam (reflected by the beam splitter) is reflected by a fixed mirror and returns to the beam splitter, and the other beam (transmitted by the beam splitter) is reflected by the movable mirror and returns to the beam splitter. The two beams are combined by the beam splitter and output as beams from interferometer. The output beams from interferometer form an interferogram showing the intensity depending on the moved position of the movable mirror, that is, the intensity depending on the difference (D) in optical path lengths between the two beams.

The optical filter 30 transmits light in a wavelength range needed for measurement, from among the output beams generated by the FTIR 20. The polarizer 40 is disposed to extract linearly polarized light having the polarization plane expressed as Y=X, from light transmitted by the optical filter 30. The PEM 50 is disposed with its main axis aligned with the Y direction. The direction of the optical axis of the polarizer 40 and the direction of the main axis of the PEM 50 are not confined to the combination given above. As the minimum requirement, the two directions should meet at an angle of 45 degrees when viewed from the Z-axis direction.

The phase difference δ of the linearly polarized light is modulated by the PEM 50. More specifically, the phase difference δ between two orthogonal components (X-direction component and Y-direction component in FIG. 3) of the linearly polarized light is modulated by the PEM 50. The phase difference δ is usually modulated with a sine curve. In accordance with the modulation of the phase difference δ, the polarization state of linearly polarized light is also modulated. As a result, the PEM 50 outputs right-handed and left-handed elliptically polarized light alternately. The sample setting portion 60 is exposed alternately to the right-handed and left-handed elliptically polarized light.

After the polarizer 40 generates an interferogram of linearly polarized light from the output beams from interferometer, the PEM 50 performs phase modulation, and the resultant light is directed to the sample setting portion 60, basically in the same manner as performed in the conventional vibrational CD spectrometer. In the present invention, however, the depolarizer 10 is additionally disposed after the sample setting portion 60. The depolarizer 10 is disposed to depolarize light transmitted through the sample setting portion 60. With the holders 16A and 16B shown in FIGS. 2A and 2B, the depolarizer 10 can be disposed such that pressure is applied to the front wedge plate 12 in the X direction and pressure is applied to the back wedge plate 14 in the direction expressed as Y=−X. Light transmitted by the depolarizer 10 is focused by the focusing lens 70 onto the detector 80, and the detector 80 detects the intensity of light.

Figure 3:
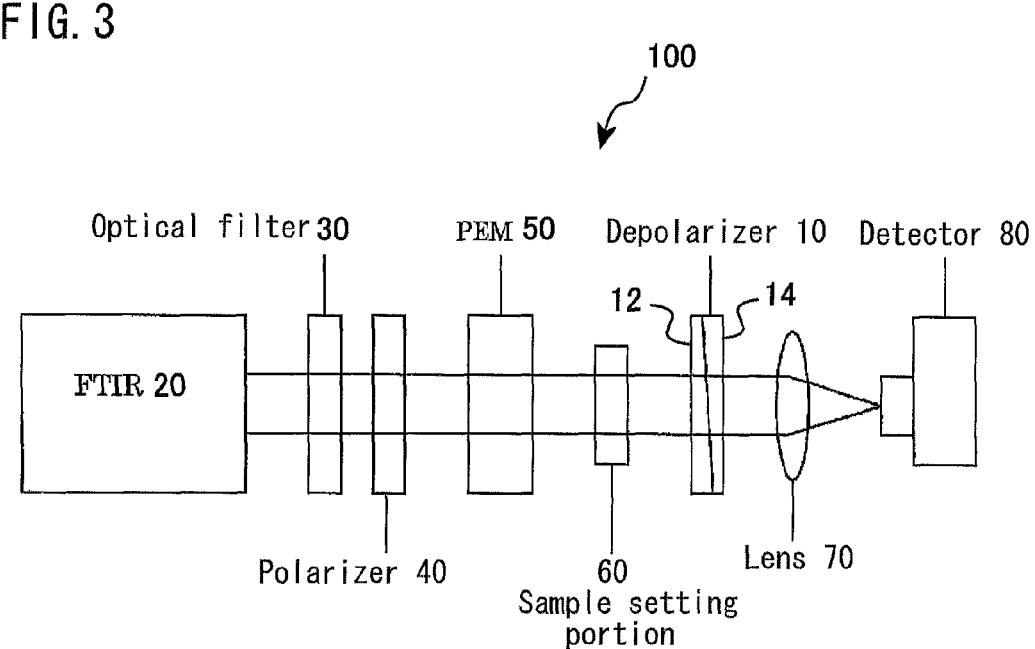
FIG. 3 is a diagram showing the entire configuration of a circular dichroism spectrometer according to a first embodiment of the present invention.

The data processing system of the CD spectrometer, which is not shown in FIG. 3, includes a pre-amplifier, a lock-in amplifier, a DC amplifier, a PEM driver, an A/D converter, and a data processor. The light intensity signal detected by the detector 80 is amplified by the pre-amplifier, and its direct-current component and alternating-current component are separately amplified. The lock-in amplifier receives a signal synchronized with the drive frequency of the PEM 50 from the PEM driver and extracts the alternating current (AC) component having the same frequency as the drive frequency from the light intensity signal. The DC amplifier extracts the direct-current (DC) component from the light intensity signal. The DC component signal and the AC component signal are quantified by an appropriate A/D converter and taken into the data processor.

The data processor calculates the ratio of the AC component to the DC component (AC/DC). The calculated value is a signal stream concerning the CD value (=ΔA) and is an interferogram rather than the CD value itself. The stream is sent to a control PC for data processing, where a Fourier transform is performed to generate a wavelength (wave number ν) spectrum. By multiplying the spectrum by the modulation amplitude δ0 with wave number ν as a parameter, the CD spectrum can be obtained as given by formula (I) below. In the formula, F[ ] expresses a Fourier transform.

$$\Delta A(\nu) = -\frac{1}{\ln 10} \cdot \delta_0(\nu) \cdot F\left[\frac{AC}{DC}\right] \qquad (1)$$

In measuring the CD value of a sample by the CD spectrometer 100 configured as described above, the following advantages are provided. In the conventional CD spectrometers, the detector receives the beam transmitted through the sample directly without depolarization. The polarization state of the beam transmitted through the sample oscillates between right-handed and left-handed circularly polarization with linearly polarization at the center. When the detector receives polarized light (such as linearly polarized light, or elliptically polarized light being an intermediate state between linearly polarized light and circularly polarized light), the polarization state is sometimes influenced by the distortion of a focusing lens or the like. When light strongly polarized in a specific direction, such as linearly polarized light or elliptically polarized light, enters, the output depends on the direction of vibration rather than the intensity. Accordingly, the difference in absorbance between right-handed and left-handed circularly polarized light cannot be accurately detected, making the measured results inaccurate.

According to the present invention, a light beam transmitted through the sample setting portion 60 is depolarized by the depolarizer 10, and then, is received by the detector 80. Since the intensity of the beam is maintained even after it is depolarized, the difference in absorbance between right-handed and left-handed circularly polarized light is maintained. The detector 80 detects the depolarized light, the signal processor processes the detected signal, and then the difference in absorbance between right-handed and left-handed circularly polarized light (CD value) can be calculated on the basis of variations in the light intensity signal. Since the detector 80 receives light depolarized by the depolarizer 10, a correctly measured CD value can be obtained without the error produced in the conventional apparatuses.

Second Embodiment

A CD spectrometer 200 according to a second embodiment of the present invention will be described next with reference to FIG. 4. The CD spectrometer 200 has the same basic configuration as the CD spectrometer 100 in the first embodiment. The same reference numerals will be used appropriately in the following description.

Figure 4:
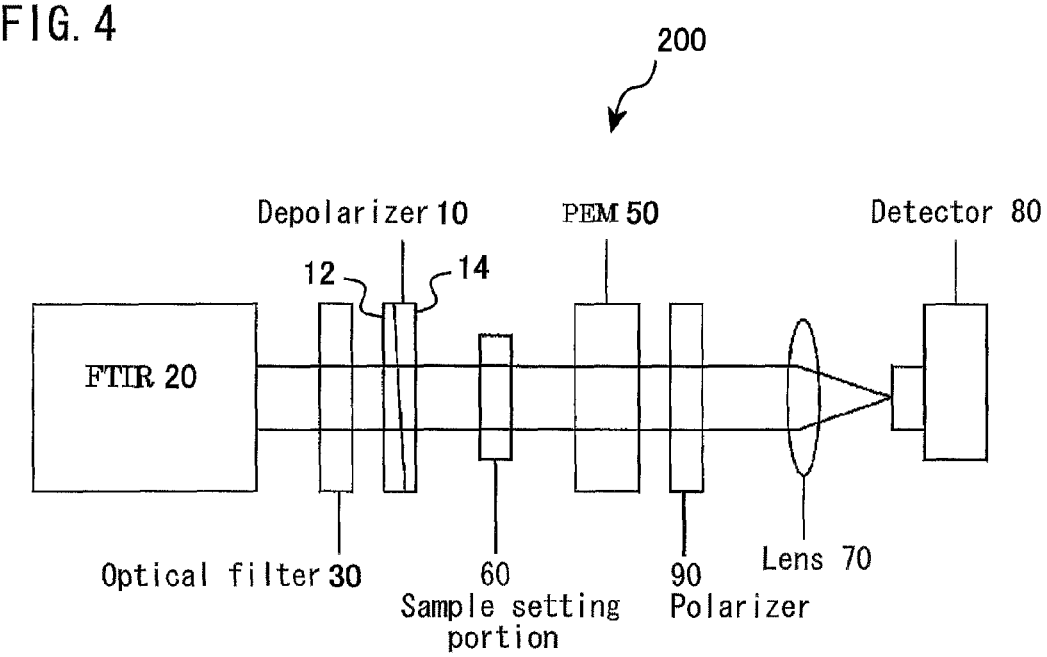
FIG. 4 is a diagram showing the entire configuration of a circular dichroism spectrometer according to a second embodiment of the present invention.

FIG. 4 shows the entire configuration of the CD spectrometer 200. The measuring optical system includes an FTIR 20, an optical filter 30, a depolarizer 10, a sample setting portion 60, a PEM 50, a polarizer 90, a focusing lens 70, and a detector 80. Those components are disposed on the optical axis of the test beam in that order.

In the present invention, one feature is that the depolarizer 10 is disposed after the optical filter 30. The depolarizer 10 is provided to depolarize light to be directed to the sample setting portion 60. With the holders 16A and 16B shown in FIGS. 2A and 2B, the depolarizer 10 can be disposed such that pressure is applied to the front wedge plate 12 in the X direction and pressure is applied to the back wedge plate 14 in the direction expressed as Y=−X.

In the optical configuration shown in FIG. 4, the pressure-applying directions C1 and C2 of the depolarizer 10 can be specified in a desired manner with respect to the direction of the main axis of the PEM 50. The pressure-applying directions C1 and C2 must meet at an angle of 45 degrees, irrespective of the direction of the main axis of the PEM. The depolarizer 10 does not place a limitation on the polarizing direction of the optical system, and the degree of freedom of the optical configuration is maintained.

The light beam brought into the unpolarized state strikes the sample setting portion 60. The sample absorbs right-handed and left-handed circularly polarized light included in the beam brought into the unpolarized state with different levels of absorbance. The polarization state of light transmitted through the sample setting portion 60 is modulated by the PEM 50. Light having a specific linear polarization is extracted by the polarizer 90 and then detected by the detector 80.

In measuring the CD value of a sample by the CD spectrometer 200 configured as described above, the following advantages are provided. In this embodiment, light directed onto the sample setting portion 60 is in the unpolarized state. This state, however, is a mixture of polarized light in a variety of vibration directions. For the sake of simplicity, the advantages will be described by using an unpolarized model containing simple polarized light components.

FIG. 5 shows variations in polarization state in CD measurement by using the unpolarized model. The unpolarized model includes a linearly polarized light component in the X-axis direction, a linearly polarized light component in the Y-axis direction, a left-handed circularly polarized light component, and a right-handed circularly polarized light component. The polarized light components have equal intensity, and the intensity of the polarized light components is expressed as 25. The beam depolarized by the depolarizer 10 corresponds to the unpolarized light model. In the sample setting portion 60, the absorbance of right-handed circularly polarized light is higher than the absorbance of the left-handed circularly polarized light, the intensity of right-handed circularly polarized light in the beam transmitted through the sample setting portion 60 is 20, and the intensity of the other polarized light components (X linearly polarized light, Y linearly polarized light, and left-handed circularly polarized light) is 23.

When the beam in the unpolarized state described above is modulated by the PEM 50, the polarized light components maintain their intensity, but their polarization states vary. For example, the X linearly polarized light component varies its polarization state cyclically from X linearly polarized light through right-handed circularly polarized light, X linearly polarized light, and left-handed circularly polarized light to X linearly polarized light, as shown in FIG. 5. The Y linearly polarized light component changes its polarization state cyclically from Y linearly polarized light, through left-handed circularly polarized light, Y linearly polarized light, and right-handed circularly polarized light to Y linearly polarized light. The left-handed circularly polarized light component changes its polarization state cyclically from left-handed circularly polarized light, through X linearly polarized light, left-handed circularly polarized light, and Y linearly polarized light to left-handed circularly polarized light. The right-handed circularly polarized light component changes its polarization state cyclically from right-handed circularly polarized light, through Y linearly polarized light, right-handed circularly polarized light, and X linearly polarized light to right-handed circularly polarized light.

If just the X linearly polarized light component is extracted by the polarizer 90 from light appearing to be unpolarized because of the varying polarization state, linearly polarized light with its intensity varying with the modulation cycle of the PEM 50 can be obtained. The detector 80 detects the intensity of the linearly polarized light. If the test beam is not directed onto the sample, the detected intensity of the linearly polarized light remains at a constant value (25). If the test beam is directed onto the sample and if a greater amount of the right-handed circularly polarized light component is absorbed, the detected intensity of linearly polarized light will alternate between 23 and 20. In other words, the signal detected by the detector 80 will include the difference in absorbance between right-handed and left-handed circularly polarized light (CD value). A CD spectrum of the sample can be obtained by calculating the ratio of the alternating current component to the direct current component (AC/DC) of the signal detected in the CD spectrometer 200 in this embodiment, by using the same data processing system as included in the CD spectrometer 100 in the first embodiment, and by performing a Fourier transform by using a control PC.

In the CD spectrometer 200 in this embodiment, when output beams produced by the FTIR 20 is polarized even slightly, the depolarizer 10 disposed before the sample setting portion 60 brings the light into the unpolarized state before the light beam strikes the sample setting portion 60. Therefore, even if the polarized state of a specific polarized light component changes because of the distortion of an optical component, such as the PEM 50 or the focusing lens 70, the effect of the change on the polarized state of the entire beam becomes minute and almost negligible. In comparison with when a light beam formed only of a component having a specific polarized state enters the PEM 50 or the focusing lens 70, the difference in absorbance between the right-handed and left-handed circularly polarized light can be detected more accurately, and the accuracy of the measured result can be improved.

In the CD spectrometer 100 and the CD spectrometer 200 in the embodiments described above, the depolarizer 10 may be switched in accordance with the measurement wave number range. For example, if a plurality of measurement wave number ranges are specified, it is advisable to prepare a plurality of depolarizers that can provide optimum phase differences δ in the individual measurement wave number ranges.

| DESCRIPTION OF REFERENCE NUMBERS | |
| --- | --- |
| 10 | Depolarizer |
| 12, 14 | Wedge plate |
| 16A, 16B | Holder (Wedge-plate holding means) |
| 22 | Fixed plate (Fixed member) |
| 28 | Pressing plate (Pressing member) |
| 40, 90 | Polarizer |
| 50 | PEM (Polarization modulator) |
| 60 | Sample setting portion |
| 70 | Focusing lens |

-continued

| DESCRIPTION OF REFERENCE NUMBERS | |
|---|---|
| 80 | Detector |
| 100, 200 | Circular dichroism spectrometer |

What is claimed is:

1. A circular dichroism spectrometer including:
a polarizer configured to transmit light having a specific linear polarization in a light beam coming from a light source;
a polarization modulator configured to generate right-handed circularly polarized light and left-handed circularly polarized light alternately by modulating the linearly polarized light;
a sample setting portion which is alternately exposed to the right-handed circularly polarized light and the left-handed circularly polarized light;
a depolarizer which is disposed after the sample setting portion to depolarize the beam reflected or transmitted by the sample setting portion; and
a detector configured to detect the intensity of the depolarized light,
wherein the depolarizer includes:
a pair of wedge-shaped plates made of an optically isotropic material, laid one on top of another such that the total thickness is constant; and wedge-plate holding means for holding the pair of wedge plates separately,
wherein the wedge-plate holding means includes a pressure-applying section for applying pressure to each of the pair of wedge plates in a direction perpendicular to the thickness direction of the pair of wedge plates,
wherein the pressure-applying direction for one of the pair of wedge plates and the pressure-applying direction for the other of the pair of wedge plates intersect at an angle of 45 degrees,
wherein the detector is configured to obtain a difference in absorbance between the right-handed circularly polarized light and the left-handed circularly polarized light in accordance with a change in the detected intensity of light.

2. A circular dichroism spectrometer according to claim 1, further including a focusing lens for focusing light disposed before the detector, wherein the depolarizer is disposed before the focusing lens.

3. A circular dichroism spectrometer including:
a depolarizer which is disposed after a light source to depolarize a light beam coming from the light source;
a sample setting portion which is exposed to the depolarized light beam;
a polarization modulator configured to modulate light reflected or transmitted by the sample setting portion;
a polarizer configured to transmit linearly polarized light having a specific polarization plane in the modulated light beam; and
a detector configured to detect the intensity of the linearly polarized light, wherein the depolarizer includes:
a pair of wedge-shaped plates made of an optically isotropic material, laid one on top of another such that the total thickness is constant; and wedge-plate holding means for holding the pair of wedge plates separately,
wherein the wedge-plate holding means includes a pressure-applying section for applying pressure to each of the pair of wedge plates in a direction perpendicular to the thickness direction of the pair of wedge plates,
wherein the pressure-applying direction for one of the pair of wedge plates and the pressure-applying direction for the other of the pair of wedge plates intersect at an angle of 45 degrees,
wherein the detector is configured to obtain a difference in absorbance between right-handed circularly polarized light and left-handed circularly polarized light in the depolarized light beam in accordance with variations in the detected intensity of light.

4. A circular dichroism spectrometer according to claim 1, wherein the depolarizer is switchable in accordance with the measurement wave number range.

5. A circular dichroism spectrometer according to claim 1, wherein the pressure-applying direction for the one of the pair of wedge plates is parallel to the direction in which the thickness of the wedge plate changes at the maximum rate.

6. A circular dichroism spectrometer according to claim 1, wherein the pressure-applying section includes a fixed member and a holding member for holding each of the pair of wedge plates, wherein the holding member is provided to be movable in the pressure-applying direction with respect to the fixed member.

7. A circular dichroism spectrometer according to claim 1, wherein the optically isotropic material is an optically isotropic crystal.

8. A circular dichroism spectrometer according to claim 1, wherein each of the pair of wedge plates has the shape of a regular octagon when viewed from the thickness direction.

9. The circular dichroism spectrometer according to claim 3, wherein the pressure-applying direction for the one of the pair of wedge plates is parallel to the direction in which the thickness of the wedge plate changes at the maximum rate.

10. The circular dichroism spectrometer according to claim 3, wherein the pressure-applying section includes a fixed member and a holding member for holding each of the pair of wedge plates, wherein the holding member is provided to be movable in the pressure-applying direction with respect to the fixed member.

11. The circular dichroism spectrometer according to claim 3, wherein the optically isotropic material is an optically isotropic crystal.

12. The circular dichroism spectrometer according to claim 3, wherein each of the pair of wedge plates has the shape of a regular octagon when viewed from the thickness direction.

13. The circular dichroism spectrometer according to claim 3, wherein the depolarizer is switchable in accordance with the measurement wave number range.

* * * * *